United States Statutory Invention Registration [19]

[11] Reg. Number: H531

Ray et al. [43] Published: Oct. 4, 1988

[54] ANILIDE HERBICIDE DERIVATIVES

[76] Inventors: John A. Ray, 3327 S. Alston Dr., Durham, N.C. 27713; Thomas N. Wheeler, 8605 Woodlawn Dr., Raleigh, N.C. 27612

[21] Appl. No.: 869,912

[22] Filed: Jun. 3, 1986

[51] Int. Cl.[4] ..... A01N 57/00; A01N 43/40; A01N 43/36; A01N 43/48

[52] U.S. Cl. ..... 71/86; 71/94; 71/95; 71/96; 71/92; 71/87; 548/414; 548/513; 548/413; 548/545; 546/23; 546/121; 548/512; 548/409

[58] Field of Search ..... 548/414, 513, 512, 409; 71/96, 86, 87

[56] References Cited

U.S. PATENT DOCUMENTS

| | | | |
|---|---|---|---|
| 3,987,057 | 10/1976 | Goddard et al. | 71/96 X |
| 4,001,272 | 1/1977 | Goddard | 71/96 X |
| 4,120,693 | 10/1978 | Goddard et al. | 71/96 |
| 4,380,466 | 4/1983 | Ishida | 71/96 |
| 4,431,822 | 2/1984 | Nagano et al. | 548/513 |

FOREIGN PATENT DOCUMENTS

| | | | |
|---|---|---|---|
| 0040849 | 12/1981 | European Pat. Off. | 548/513 |
| 0049508 | 4/1982 | European Pat. Off. . | |
| 0061741 | 10/1982 | European Pat. Off. . | |
| 0068822 | 1/1983 | European Pat. Off. . | |
| 0077938 | 5/1983 | European Pat. Off. . | |
| 0083055 | 7/1983 | European Pat. Off. . | |
| 0126419 | 11/1984 | European Pat. Off. . | |
| 0092760 | 8/1978 | Japan | 548/471 |
| 54-019965 | 2/1979 | Japan . | |
| 57-149267 | 9/1982 | Japan . | |
| 59-108767 | 6/1984 | Japan . | |
| 59-155358 | 9/1984 | Japan . | |
| 228494 | 11/1985 | Japan . | |
| 246392 | 12/1985 | Japan . | |

*Primary Examiner*—John F. Terapane
*Assistant Examiner*—J. E. Thomas

[57] ABSTRACT

Novel anilide derivatives of the formula

Z—Ar wherein

Z is a heterocyclic ring system attached to Ar through a ring nitrogen atom in Z, and Ar is a substituted phenyl ring, exhibit good control of broadleaf weeds and safety to important crops at low application rates.

38 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ANILIDE HERBICIDE DERIVATIVES

FIELD OF THE INVENTION

This invention relates to novel anilide herbicide derivatives which exhibit good control of broadleaf weeds and safety to important crops at low application rates.

BACKGROUND OF THE INVENTION

N-aryl-3,4,5,6 tetrahydrophthalimides are known to be useful as herbicides. See, for example, U.S. Pat. No. 4,001,272 and Japanese published patent application No. 54019965 published July 12, 1977.

Herbicidal tetrahydrophthalimides substituted at the $C_5$ position by, among others, alkoxy, amino, carboxyl, or thio functions have been disclosed in European published patent applications No. 061741 published Oct. 6, 1982 (Sumitomo), No. 049508 published Apr. 14, 1982 (Mitsubishi) No. 077438 published May 4, 1983 (Mitsubishi), No. 083055 published July 6, 1983 (Sumitomo), No. 126419 published Nov. 28, 1984 (Sumitomo), and Japanese application No. 9155358 published Sept. 4, 1984 (Sumitomo).

SUMMARY OF THE INVENTION

In its broad aspect the invention relates to novel anilide compounds, herbicidal compositions containing the same, and processes for their preparation and use. The compounds of this invention can be represented by the following generic formula:

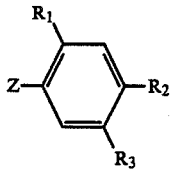

wherein the various substituents are defined hereinafter.

DETAILED DISCUSSION OF THE INVENTION

This invention relates to anilide compounds having the structure:

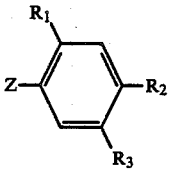

wherein:

$R_1$ and $R_2$ contain not more than 10 aliphatic carbon atoms and are independently:

hydrogen, halogen, $C_1$–$C_3$) alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl groups;

$R_3$ is a substituted heteroatom or a substituted carbon atom, or a substituted or unsubstituted, branched or straight chain containing 2 or more carbon atoms or heteroatoms in any combination;

Z is:

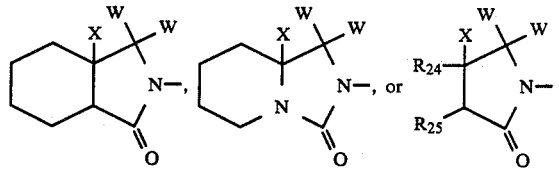

wherein:

$R_{24}$ and $R_{25}$ : independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenylthio, alkynylthio, cycloalkylthio, cycloalkenylthio, alkoxycarbonylalkoxy, alkoxycarbonylalkylthio, haloalkoxy, haloalkylthio, alkoxyalkoxy, alkylthioalkoxy (e.g., —$OCH_2SCH_3$), alkoxyalkylthio, alkylthioalkylthio, cyanoalkoxy, alkylcarbonylalkoxy, alkylcarbonylalkylthio, phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by up to two alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by up to two alkyl, alkynyl, phenyl, or phenyl substituted by one or more halogen, lower alkyl, lower alkoxy, cyano, nitro, alkylthio, or haloalkyl groups, aminocarbonylalkylthio wherein the amino group may be substituted by up to two alkyl, alkenyl, phenyl, or phenyl substituted by one or more halogen, lower alkyl, lower alkoxy, cyano, nitro, alkylthio, or haloalkyl groups, a five or six-member ring containing one or two oxygen, nitrogen, or sulfur atoms; and X contains not more than 10 aliphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

In the above formula, $R_3$ is preferably

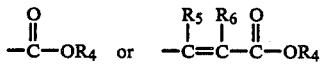

wherein:

$R_4$ contains not more than 10 aliphatic carbon atoms and is:

hydrogen, $C_1$–$C_{10}$ alkyl, alkenyl cycloalkyl, cycloalkenyl, or alkynyl, alkoxycarbonylalkyl e.g., —$CH_2CO_2Et$), alkoxycarbonyl (e.g.,

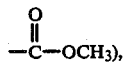

alkylcarbonyl alkenylcarbonyl, alkynylcarbonyl, cycloalkylcarbonyl, phenyl, phenylcarbonyl or phenoxycarbonyl wherein the phenyl ring of each may be substituted by one or more halogen, lower alkyl, lower alkoxy, cyano, nitro, alkylthio, or haloalkyl groups, and $R_5$ and $R_6$ are independently hydrogen or $C_1$–$C_3$ alkyl.

$R_3$ can also be —$OR_4$, wherein $R_4$ is as defined above.

$R_3$ can also be

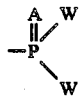

wherein

A is oxygen or sulfur and W is as defined above.

$R_3$ can also be

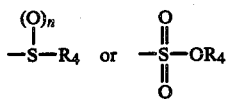

wherein n is an integer from 0–2 and $R_4$ as is defined above.

$R_3$ can also be

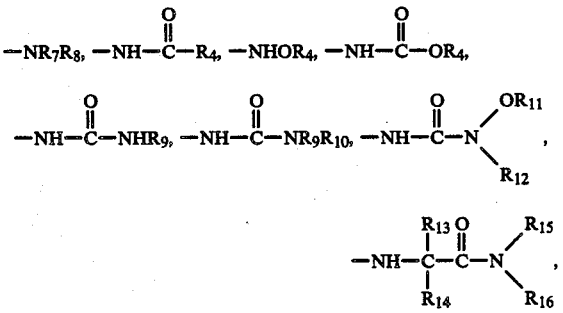

wherein $R_4$ is as defined above, and wherein:

$R_7$ and $R_8$ are independently hydrogen, $C_1$–$C_6$ alkyl, alkenyl, alkynyl, cycloakyl, mono-or dialkylaminocarbonylalkyl or, taken together, $R_7$ and $R_8$ form a five- or six-membered heterocyclic ring containing one to three oxygen, nitrogen, or sulfur atoms in any combination;

$R_9$ and $R_{10}$ are independently hydrogen, $C_1$–$C_4$ alkyl or, taken together, $R_9$ and $R_{10}$ form a five- or six-membered ring;

$R_{11}$ is $C_1$–$C_3$ alkyl;

$R_{12}$ is hydrogen or $C_1$–$C_3$alkyl;

$R_{13}$ and $R_{14}$ are independently hydrogen or $C_1$–$C_3$ alkyl; and $R_{15}$ and $R_{16}$ are independently hydrogen, $C_1$–$C_3$ alkyl, or $C_1$–$C_3$ alkoxy;

$R_3$ can also be

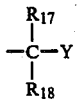

wherein $R_{17}$ and $R_{18}$ are independently hydrogen $C_1$–$C_8$ alkyl, or halogen; and Y contains not more than 10 aliphatic carbon atoms and is:

hydrogen, halogen, cyano, alkyl, cyloalkyl, cycloalkyl alkyl, alkenyl, cycloalkenyl, cycloalkenyl alkyl, alkynyl, alkoxy, alkenyloxy, alkynyloxy, cycloalkyloxy, cycloalkenyloxy, alkoxycarbonylalkoxy, alkoxycarbonylalkylthio, alkoxycarbonyloxy, alkoxycarbonylamino, alkylthiocarbonyloxy, alkylaminothiocarbonyloxy, haloalkoxy, haloalkylthio, alkoxyalkoxy, alkylthioalkoxy, alkoxyalkylthio, alkylthioalkylthio, cyanoalkoxy, alkylcarbonylalkoxy, cycloalkoxycarbonylalkoxy, alklycarbonylalkylthio, alkoxycarbonylalkylamino, alkoxycarbonylalkyl alkylamino, alkylsulfinyl, alkylsulfonyl, alkoxycarbonylalkylsufinyl, alkoxycarbonylalkylsulfonyl, alkylcarbonylalkylamino, phenoxy, phenylthio, phenylcarbonylalkoxy, phenoxycarbonylalkoxy, phenylcarbonylalkylthio, phenoxycarbonylalkylthio, or phenylcarbonylalkylamino wherein the phenyl ring in each may be substituted by one or more halogen, lower alkyl, lower alkoxy, cyano, nitro, alkylthio, or haloalkyl groups, phenylsulfinyl or phenylsulfonyl wherein the phenyl ring in either may be substituted by one or more halogen, lower alkyl, lower alkoxy, cyano, nitro, alkylthio, or haloalkyl groups, amino substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group is substituted by one or more alkyl, alkenyl, phenyl or phenyl substituted by one or more halogen, lower alkyl, lower alkoxy, cyano, nitro, alkylthio, or haloalkyl groups, aminocarbonylalkylthio wherein the amino group is substituted by one or more alkyl, alkenyl, phenyl, or phenyl substituted by one or more halogen, lower alkyl, lower alkoxy, cyano, nitro, alkylthio, or haloalkyl groups, aminocarbonylalkylamino wherein each of the amino groups is independently substituted by one or more alkyl, alkenyl, alkynyl, phenyl or phenyl substituted by one or more halogen, lower alkyl, lower alkoxy, cyano, nitro, alkylthio, or haloalkyl groups, or any of the following functional groups:

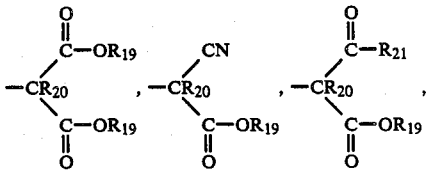

-continued

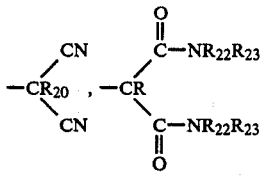

wherein:

$R_{19}$ is $C_1$–$C_6$ alkyl, cycloalkyl, alkenyl, alkynyl, or cycloakenyl;

$R_{20}$ and $R_{21}$ are independently hydrogen, $C_1$–$C_6$ alkyl, cycloalkyl, alkenyl, alkynyl, cycloalkenyl, phenyl, or phenyl substituted by one or more halogen, lower alkyl, lower alkoxy, cyano, nitro, alkylthio, or haloalkyl groups, $R_{22}$ and $R_{23}$ are independently hydrogen, $C_1$–$C_6$ alkyl, cycloalkyl, alkenyl, alkynyl, or cycloalkenyl;

or wherein Y is any five- or six-membered heterocycle containing from one to three oxygen, nitrogen, or sulfur atoms.

The novel anilide herbicides of this invention are illustrated by, but not limited to, the compounds shown in the following charts A–C.

CHART A

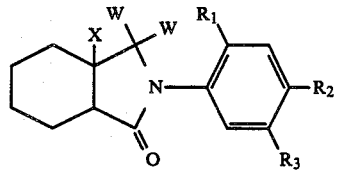

| X | W | $R_1$ | $R_2$ | $R_3$ |
|---|---|---|---|---|
| Cl | $OCH_3$ | F | Cl | $-OCH(CH_3)_2$ |
| Cl | $OCH_3$ | F | Cl | $-CH_2OCH(CH_3)_2$ |
| Cl | $OCH_3$ | F | Cl | $-CO_2CH_3$ |
| Cl | $OCH_3$ | F | Cl | $-\overset{O}{\overset{\|\|}{P}}(OCH_3)_2$ |
| Cl | $OCH_3$ | F | Cl | 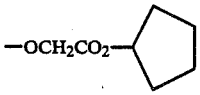 |
| Cl | $OCH_3$ | F | Cl | $-CH{\equiv}CHCO_2CH_3$ |
| Cl | $OCH_3$ | F | Cl | $-NH\overset{CH_2CH_3}{\overset{\|}{C}}HCONHCH(CH_3)_2$ |
| Cl | $OCH_3$ | F | Cl | $-CH_2OCH_2CO_2CH_3$ |
| Cl | $OCH_3$ | F | Cl | $-CH_2SCH_2CH_2$ |
| Cl | $OCH_3$ | F | Cl | $-SCH_2CO_2CH_2$ |
| Cl | $OCH_3$ | F | Cl | $-SCH_2CH_3$ |
| Cl | $OCH_3$ | F | Cl | $-CH_2OCH_2C{\equiv}CH$ |
| OH | $OCH_3$ | F | Cl | $-OCH(CH_3)_2$ |
| OH | $OCH_3$ | F | Cl | $-CH_2OCH(CH_3)_2$ |
| OH | $OCH_3$ | F | Cl | $-CO_2CH_3$ |
| OH | $OCH_3$ | F | Cl | $-\overset{O}{\overset{\|\|}{P}}(OCH_3)_2$ |
| $-\overset{O}{\overset{\|\|}{O}}CCH_3$ | $OCH_3$ | F | Cl | $-OCH(CH_3)_2$ |
| $-\overset{O}{\overset{\|\|}{O}}CCH_3$ | $OCH_3$ | F | Cl | $-CH_2OCH(CH_3)_2$ |
| $-\overset{O}{\overset{\|\|}{O}}CCH_3$ | $OCH_3$ | F | Cl | $-CO_2CH_3$ |
| $-\overset{O}{\overset{\|\|}{O}}CCH_3$ | $OCH_3$ | F | Cl | $-\overset{O}{\overset{\|\|}{P}}(OEt)_2$ |
| $-\overset{O}{\overset{\|\|}{O}}COCH_3$ | $OCH_3$ | F | Cl | $-OCH(CH_3)_2$ |
| $-\overset{O}{\overset{\|\|}{O}}COCH_3$ | $OCH_3$ | F | Cl | $-CH_2OCH(CH_3)_2$ |

CHART A-continued

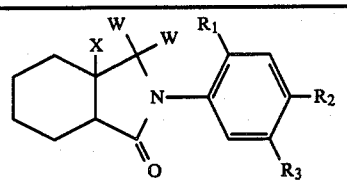

| X | W | $R_1$ | $R_2$ | $R_3$ |
|---|---|---|---|---|
| $-\overset{O}{\overset{\|\|}{S}}CH_2CH_3$ | $OCH_3$ | F | Cl | $-OCH(CH_3)_2$ |
| $-\overset{O}{\overset{\|\|}{S}}COCH_2CH_3$ | $OCH_3$ | F | Cl | $-OCH(CH_3)_2$ |
| $-OCH_3$ | $OCH_3$ | F | Cl | $-OCH(CH_3)_2$ |
| $-OCH_3$ | $OCH_3$ | F | Cl | $-CH_2OCH(CH_3)_2$ |
| $-OCH_3$ | $OCH_3$ | F | Cl | $-CO_2CH_3$ |
| $-OCH_3$ | $OCH_3$ | F | Cl | $-\overset{O}{\overset{\|\|}{P}}(OCH_3)_2$ |
| $-OCH_2CH{\equiv}CH_2$ | $OCH_3$ | F | Cl | $-OCH(CH_3)_2$ |
| $-OCH_2C{\equiv}CH$ | $OCH_3$ | F | Cl | $-OCH(CH_3)_2$ |
| $-OCH_2C{\equiv}CH$ | $OCH_3$ | F | Cl | $-CH_2OCH(CH_3)_2$ |
| $-NH_2$ | $OCH_3$ | F | Cl | $-OCH(CH_3)_2$ |
| $-NH_2$ | $OCH_3$ | F | Cl | $-CH_2OCH(CH_3)_2$ |
| $-NHCH_3$ | $OCH_3$ | F | Cl | $-OCH(CH_3)_2$ |
| $-N(CH_3)_2$ | $OCH_3$ | F | Cl | $-OCH(CH_3)_2$ |
| $-N(CH_3)_2$ | $OCH_3$ | F | Cl | $-CH_2OCH(CH_3)_2$ |
| $-SH$ | $OCH_3$ | F | Cl | $-OCH(CH_3)_2$ |
| $-SCH_3$ | $OCH_3$ | F | Cl | $-OCH(CH_3)_2$ |
| $-SCH_3$ | $OCH_3$ | F | Cl | $-CH_2OCH(CH_3)_2$ |
| $-SCH_3$ | $OCH_3$ | F | Cl | $-CO_2CH_3$ |
| $-SCH_3$ | $OCH_3$ | F | Cl | $-\overset{O}{\overset{\|\|}{P}}(OCH_3)_2$ |
| $-SCH_2CH{=}CH_2$ | $OCH_3$ | F | Cl | $-OCH(CH_3)_2$ |
| $-\overset{O}{\overset{\|\|}{S}}CH_2CH_3$ | $OCH_3$ | F | Cl | $-OCH(CH_3)_2$ |
| $-SO_2CH_2CH_3$ | $OCH_3$ | F | Cl | $-OCH(CH_3)_2$ |
| Cl | $-OCH_2CH_2O-$ | F | Cl | $-OCH(CH_3)_2$ |
| Cl | $-OCH_2CH_2O-$ | F | Cl | $-CH_2OCH(CH_3)_2$ |
| Cl | $-OCH_2CH_2O-$ | F | Cl | $-CO_2CH_3$ |
| Cl | $-OCH_2CH_2O-$ | F | Cl | $-\overset{O}{\overset{\|\|}{P}}(OCH_3)_2$ |
| Cl | $-SCH_2CH_2S-$ | F | Cl | $-OCH(CH_3)_2$ |
| Cl | $-SCH_2CH_2S-$ | F | Cl | $-CH_2OCH(CH_3)_2$ |
| Cl | $-SCH_2CH_2S-$ | F | Cl | $-CO_2CH_3$ |
| Cl | $-SCH_2CH_2S-$ | F | Cl | $-\overset{O}{\overset{\|\|}{P}}(OCH_3)_2$ |
| Cl | $-OCH_2CH{=}CH_2$ | F | Cl | $-OCH(CH_3)_2$ |
| Cl | $-OCH_2C{\equiv}CH$ | F | Cl | $-CH_2OCH(CH_3)_2$ |
| Cl | $-SCH_2CH_3$ | F | Cl | $-OCH(CH_3)_2$ |
| Cl | $-SCH_2CH_3$ | F | Cl | $-CH_2OCH(CH_3)_2$ |
| Cl | $-SCH_2CH_3$ | F | Cl | $-CO_2CH_3$ |
| Cl | $-SCH_2CH_3$ | F | Cl | $-\overset{O}{\overset{\|\|}{P}}(SCH_2CH_3)_2$ |
| $-SCH_2CH_3$ | $-SCH_2CH_3$ | F | Cl | $-OCH(CH_3)_2$ |
| $-SCH_2CH_3$ | $-SCH_2CH_3$ | F | Cl | $-CH_2OCH(CH_3)_2$ |
| $-SCH_2CH_3$ | $-SCH_2CH_3$ | F | Cl | $-CO_2CH_3$ |
| Cl | $NH_2$ | F | Cl | $-OCH(CH_3)_2$ |
| Cl | $-N(CH_3)_2$ | F | Cl | $-OCH(CH_3)_2$ |

CHART A-continued

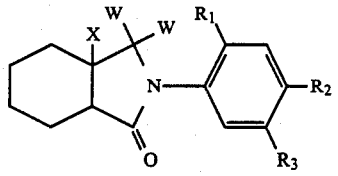

| X | W | $R_1$ | $R_2$ | $R_3$ |
|---|---|---|---|---|
| Cl | $-OCH_2CO_2CH_3$ | F | Cl | $-OCH(CH_3)_2$ |
| Cl | $-OCH_2CO_2CH_3$ | F | Cl | $-CH_2OCH(CH_3)_2$ |
| Cl | $-SCH_2CO_2CH_3$ | F | Cl | $-OCH(CH_3)_2$ |
| Cl | $-NHCH_2CO_2CH_3$ | F | Cl | $-OCH(CH_3)_2$ |
| Cl | $-OCH_2CH_2Cl$ | F | Cl | $-CH_2OCH(CH_3)_2$ |
| Cl | $-SCH_2CH_2Cl$ | F | Cl | $-CO_2CH_3$ |
| Cl | $-OCH_2OCH_3$ | F | Cl | $-OCH(CH_3)_2$ |
| Cl | $-OCH_2SCH_3$ | F | Cl | $-CH_2OCH(CH_3)_2$ |
| Cl | $-SCH_2CH_2OCH_3$ | F | Cl | $-OCH(CH_3)_2$ |
| Cl | $-SCH_2CH_2SCH_3$ | F | Cl | $-OCH(CH_3)_2$ |
| Cl | $-OCH_2CH_2CN$ | F | Cl | $-CH_2OCH(CH_3)_2$ |
| Cl | $-OCH_2\overset{O}{\overset{\|\|}{C}}CH_3$ | F | Cl | $-OCH(CH_3)_2$ |
| Cl | $-SCH_2CH_2\overset{O}{\overset{\|\|}{C}}CH_3$ | F | Cl | $-OCH(CH_3)_2$ |
| Cl | $-NHCH_2CH_2NH-$ | F | Cl | $-OCH(CH_3)_2$ |
| Cl | $-NHCH_2CH_2NH-$ | F | Cl | $-CH_2OCH(CH_3)_2$ |
| Cl | $-OCH_2CH_2S-$ | F | Cl | $-OCH(CH_3)_2$ |
| Cl | $-OCH_2CH_2S-$ | F | Cl | $-CH_2OCH(CH_3)_2$ |
| Cl | $-OCH_2CH_2S-$ | F | Cl | $-CO_2CH_3$ |
| Cl | $-OCH_2CH_2S-$ | F | Cl | $-OCH_2CO_2-$ 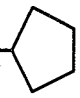 |
| Cl | $-OCH_2CH_2NH-$ | F | Cl | $-OCH(CH_3)_2$ |
| Cl | $-OCH_2CH_2NH-$ | F | Cl | $-CH_2OCH(CH_3)_2$ |
| Cl | $-NHCH_2CH_2S-$ | F | Cl | $-OCH(CH_3)_2$ |
| Cl | $-NHCH_2CH_2S-$ | F | Cl | $-CH_2OCH(CH_3)_2$ |
| Cl | $-OCH_2CH_3$ | H | Cl | $-OCH(CH_3)_2$ |
| Cl | $-OCH_2CH_3$ | H | Cl | $-CH_2OCH(CH_3)_2$ |
| Cl | $-OCH_2CH_3$ | H | Cl | $-CO_2CH_2CH_3$ |
| Cl | $-OCH_2CH_3$ | Cl | Cl | $-OCH(CH_3)_2$ |
| Cl | $-OCH_2CH_3$ | Cl | Cl | $-CH_2OCH(CH_3)_2$ |
| Cl | $-OCH_2CH_3$ | Cl | Cl | $-CO_2CH_2CH_3$ |
| Cl | $-OCH_2CH_3$ | Cl | Cl | $-CH{=}CH-\overset{O}{\overset{\|\|}{C}}-OEt$ |
| Cl | $-OCH_2CH_3$ | Cl | Cl | $-OCH_2\overset{O}{\overset{\|\|}{C}}-O-$ 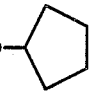 |
| Cl | $-OCH_2CH_2O-$ | Cl | Cl | $-OCH(CH_3)_2$ |
| Cl | $-OCH_2CH_2O-$ | Cl | Cl | $-CH_2OCH(CH_3)_2$ |
| Cl | $-OCH_2CH_2S-$ | Cl | Cl | $-OCH(CH_3)_2$ |
| Cl | $-SCH_2CH_2S-$ | Cl | Cl | $-OCH(CH_3)_2$ |
| Cl | $-SCH_2CH_2S-$ | Cl | Cl | $-CH_2OCH(CH_3)_2$ |
| Cl | $-OCH_2CH_3$ | F | H | $-OCH(CH_3)_2$ |
| Cl | $-OCH_2CH_3$ | F | H | $-CH_2OCH(CH_3)_2$ |
| Cl | $-OCH_2CH_3$ | F | H | $-CO_2CH_3$ |
| Cl | $-OCH_2CH_3$ | F | H | $-OCH_2\overset{O}{\overset{\|\|}{C}}-O-$ 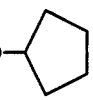 |
| Cl | $-OCH_2CH_3$ | F | H | $-CH{=}CH-CO_2CH_3$ |
| Cl | $-OCH_2CH_3$ | F | F | $-OCH(CH_3)_2$ |
| Cl | $-OCH_2CH_3$ | F | F | $-CH_2OCH(CH_3)_2$ |
| Cl | $-OCH_2CH_3$ | F | F | $-CO_2CH_3$ |

CHART A-continued

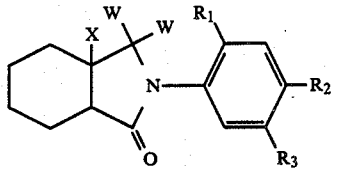

| X | W | $R_1$ | $R_2$ | $R_3$ |
|---|---|---|---|---|
| Cl | $-OCH_2CH_3$ | F | Br | $-OCH(CH_3)_2$ |
| Cl | $-OCH_2CH_3$ | F | Br | 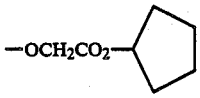 |
| Cl | $-OCH_2CH_3$ | F | Br | $-CH_2OCH(CH_3)_2$ |
| Cl | $-OCH_2CH_3$ | F | Cl | $-CH_2C{\equiv}CH$ |
| Cl | $-OCH_2CH_3$ | F | Cl | 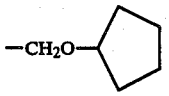 |
| Cl | $-OCH_2CH_3$ | F | Cl | $-CH_2OCH_2C{\equiv}CH$ |
| Cl | $-OCH_2CH_3$ | F | Cl | $-CH_2OPh$ |
| Cl | $-OCH_2CH_3$ | F | Cl | $-CHF_2$ |
| Cl | $-OCH_2CH_3$ | F | Cl | $-CH_2Br$ |
| Cl | $-OCH_2CH_3$ | F | Cl | $-CF_3$ |
| Cl | $-OCH_2CH_3$ | F | Cl | 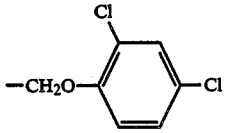 |
| Cl | $-OCH_2CH_3$ | F | Cl | 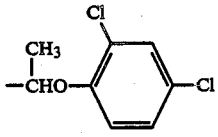 |
| Cl | $-OCH_2CH_3$ | F | Cl | 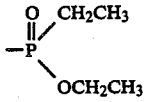 |
| Cl | $-OCH_2CH_3$ | F | Cl | 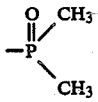 |
| Cl | $-OCH_2CH_3$ | F | Cl | 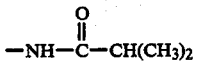 |
| Cl | $-OCH_2CH_3$ | F | Cl | $-NHCO_2CH_2CH_3$ |
| Cl | $-OCH_2CH_3$ | F | Cl | $-NHOCH_2CH_3$ |
| Cl | $-OCH_2CH_3$ | F | Cl | 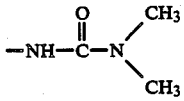 |
| Cl | $OCH_3$ | F | Cl | $-CH_2CH(CO_2CH_2CH_3)_2$ |
| Cl | $OCH_3$ | F | Cl | $-CH_2CH(CN)(CO_2CH_3)$ |
| Cl | $OCH_3$ | F | Cl | $-CH_2CH(COCH_3)(CO_2CH_3)$ |
| Cl | $OCH_3$ | F | Cl | $-CH_2CH(CON(CH_3)_2)_2$ |
| Cl | $OCH_3$ | F | $CH_3$ | $-OCH(CH_3)_2$ |
| Cl | $OCH_3$ | F | $OCH_3$ | $-OCH(CH_3)_2$ |
| Cl | $OCH_3$ | F | OPh | $-OCH(CH_3)_2$ |

CHART A-continued

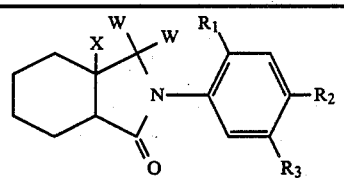

| X | W | $R_1$ | $R_2$ | $R_3$ |
|---|---|---|---|---|
| Cl | $OCH_3$ | F | 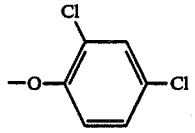 | $-OCH(CH_3)_2$ |
| Cl | $OCH_3$ | F | $-OCH_2Ph$ | $-OCH(CH_3)_2$ |
| Cl | $OCH_3$ | F | $CF_3$ | $-OCH(CH_3)_2$ |

CHART B

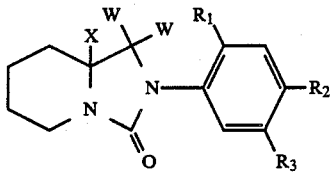

| X | W | $R_1$ | $R_2$ | $R_3$ |
|---|---|---|---|---|
| Cl | $OCH_2CH_3$ | F | Cl | $-OCH(CH_3)_2$ |
| Cl | $OCH_2CH_3$ | F | Cl | $-CH_2OCH(CH_3)_2$ |
| Cl | $OCH_2CH_3$ | F | Cl | $-CO_2CH_3$ |
| Cl | $OCH_2CH_3$ | F | Cl | $-\overset{O}{\overset{\|\|}{P}}(OCH_2CH_3)_2$ |
| Cl | $OCH_2CH_3$ | F | Cl | 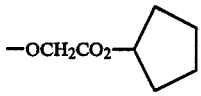 |
| Cl | $OCH_2CH_3$ | F | Cl | $-CH{=}CHCO_2CH_3$ |
| Cl | $OCH_2CH_3$ | F | Cl | $-NHCH(CH_2CH_3)CHNHCH(CH_3)_2$ |
| Cl | $OCH_2CH_3$ | F | Cl | $-CH_2OCH_2CO_2CH_2C{\equiv}CH$ |
| Cl | $OCH_2CH_3$ | F | Cl | $-CH_2SCH_2CH_3$ |
| Cl | $OCH_2CH_3$ | F | Cl | $-CH_2OCH_2C{\equiv}CH$ |
| OH | $OCH_2CH_3$ | F | Cl | $-OCH(CH_3)_2$ |
| OH | $OCH_2CH_3$ | F | Cl | $-CH_2OCH(CH_3)_2$ |
| OH | $OCH_2CH_3$ | F | Cl | $-CO_2CH_2CH_3$ |
| $-O\overset{O}{\overset{\|\|}{C}}CH_3$ | $OCH_2CH_3$ | F | Cl | $-OCH(CH_3)_2$ |
| $-O\overset{O}{\overset{\|\|}{C}}CH_3$ | $OCH_2CH_3$ | F | Cl | $-CH_2OCH(CH_3)_2$ |
| $-O\overset{O}{\overset{\|\|}{C}}OCH_3$ | $OCH_2CH_3$ | F | Cl | $-OCH(CH_3)_2$ |
| $-S\overset{O}{\overset{\|\|}{C}}CH_2CH_3$ | $OCH_2CH_3$ | F | Cl | $-OCH(CH_3)_2$ |
| $-OCH_3$ | $OCH_2CH_3$ | F | Cl | $-OCH(CH_3)_2$ |
| $-OCH_3$ | $OCH_2CH_3$ | F | Cl | $-CH_2OCH(CH_3)_2$ |
| $-OCH_2C{\equiv}CH$ | $OCH_2C{\equiv}CH$ | F | Cl | $-OCH(CH_3)_2$ |

-continued

CHART B

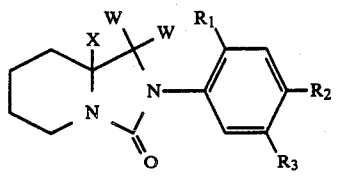

| X | W | $R_1$ | $R_2$ | $R_3$ |
|---|---|---|---|---|
| $-NH_2$ | $OCH_2CH_3$ | F | Cl | $-OCH(CH_3)_2$ |
| $-N(CH_3)_2$ | $OCH_2CH_3$ | F | Cl | $-OCH(CH_3)_2$ |
| $-SCH_2CH_3$ | $-OCH_2CH_3$ | F | Cl | $-OCH(CH_3)_2$ |
| $-SCH_2CH_3$ | $-OCH_2CH_3$ | F | Cl | $-CH_2OCH(CH_3)_2$ |
| $-SCH_2CH_3$ | $-OCH_2CH_3$ | F | Cl | $-CH_2SCH(CH_3)_2$ |
| Cl | $-OCH_2CH_2O-$ | F | Cl | $-OCH(CH_3)_2$ |
| Cl | $-OCH_2CH_2O-$ | F | Cl | $-CH_2OCH(CH_3)_2$ |
| Cl | $-SCH_2CH_2S-$ | F | Cl | $-OCH(CH_3)_2$ |
| Cl | $-SCH_2CH_2S-$ | F | Cl | $-CH_2OCH(CH_3)_2$ |
| Cl | $-SHC_2CH_2S-$ | F | Cl | $-CO_2CH_3$ |
| Cl | $-SCH_2CH_3$ | F | Cl | $-OCH(CH_3)_2$ |
| Cl | $-SCH_2CH_3$ | F | Cl | $-CH_2OCH(CH_3)_2$ |
| $-SCH_2CH_3$ | $-SCH_2CH_3$ | F | Cl | $-OCH(CH_3)_2$ |
| Cl | $-NH_2$ | F | Cl | $-OCH(CH_3)_2$ |
| Cl | $-N(CH_3)_2$ | F | Cl | $-OCH(CH_3)_2$ |
| Cl | $-OCH_2CO_2CH_3$ | F | Cl | $-OCH(CH_3)_2$ |
| Cl | $-SCH_2CO_2CH_3$ | F | Cl | $-OCH(CH_3)_2$ |
| Cl | $-NHCH_2CH_2NH-$ | F | Cl | $-OCH(CH_3)_2$ |
| Cl | $-OCH_2CH_3$ | H | Cl | $-OCH(CH_3)_2$ |
| Cl | $-OCH_2CH_3$ | H | Cl | $-CH_2OCH(CH_3)_2$ |
| Cl | $-OCH_2CH_3$ | Cl | Cl | $-OCH(CH_3)_2$ |
| Cl | $-OCH_2CH_3$ | Cl | Cl | $-CH_2OCH(CH_3)_2$ |
| Cl | $-SCH_2CH_2S-$ | Cl | Cl | $-OCH(CH_3)_2$ |
| Cl | $-SCH_2CH_2S-$ | Cl | Cl | $-CH_2OCH(CH_3)_2$ |
| Cl | $-OCH_2CH_3$ | H | Cl | $-OCH(CH_3)_2$ |
| Cl | $-OCH_2CH_3$ | H | Cl | $-CH_2OCH(CH_3)_2$ |
| Cl | $-OCH_2CH_3$ | H | Cl | $-CH_2SCH(CH_3)_2$ |
| Cl | $-OCH_2CH_3$ | H | Cl | $-CO_2CH_3$ |
| Cl | $-OCH_2CH_3$ | H | Cl | 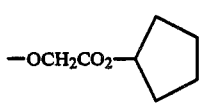 |
| Cl | $-OCH_2CH_3$ | H | Cl | 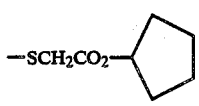 |

Chart C

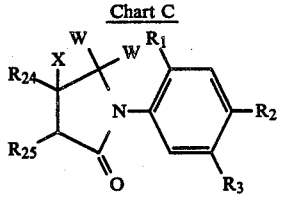

| X | W | $R_1$ | $R_2$ | $R_3$ | $R_{24}$ | $R_{25}$ |
|---|---|---|---|---|---|---|
| Cl | $OCH_2CH_3$ | F | Cl | $-OCH(CH_3)_2$ | $CH_3$ | H |
| Cl | $OCH_2CH_3$ | F | Cl | $-CH_2OCH(CH_3)_2$ | $CH_3$ | H |
| Cl | $OCH_2CH_3$ | F | Cl | $-CO_2CH_3$ | $CH_3$ | H |
| Cl | $OCH_2CH_3$ | F | Cl | $-\overset{O}{\overset{\|\|}{P}}(OCH_2CH_3)_2$ | $CH_3$ | H |
| Cl | $OCH_2CH_3$ | F | Cl | $-OCH(CH_3)_2$ | $CH_3$ | $CH_3$ |
| Cl | $OCH_2CH_3$ | F | Cl | $-CH_2OCH(CH_3)_2$ | $CH_3$ | $CH_3$ |
| Cl | $OCH_2CH_3$ | F | Cl | $-CO_2CH_3$ | $CH_3$ | $CH_3$ |

-continued

Chart C

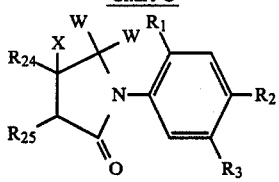

| X | W | $R_1$ | $R_2$ | $R_3$ | $R_{24}$ | $R_{25}$ |
|---|---|---|---|---|---|---|
| Cl | $OCH_2CH_3$ | F | Cl | $-\overset{O}{\overset{\|\|}{P}}(OCH_2CH_3)_2$ | $CH_3$ | $CH_3$ |
| $-\overset{O}{\overset{\|\|}{C}}OCH_3$ | $OCH_2CH_3$ | F | Cl | $-OCH(CH_3)_2$ | $CH_3$ | $CH_3$ |
| $-\overset{O}{\overset{\|\|}{C}}OCOCH_3$ | $OCH_2CH_3$ | F | Cl | $-OCH(CH_3)_2$ | $CH_3$ | $CH_3$ |
| $-OCH_3$ | $-OCH_2CH_3$ | F | Cl | $-OCH(CH_3)_2$ | $CH_3$ | $CH_3$ |
| $-OCH_3$ | $-OCH_2CH_3$ | F | Cl | $-CH_2CH(CH_3)_2$ | $CH_3$ | $CH_3$ |
| $-OCH_2C{\equiv}CN$ | $-OCH_2C{\equiv}CH$ | F | Cl | $-OCH(CH_3)_2$ | $CH_3$ | $CH_3$ |
| $-SCH_3$ | $-OCH_2CH_3$ | F | Cl | $-OCH(CH_3)_2$ | $CH_3$ | $CH_3$ |
| Cl | $-OCH_2CH_2O-$ | F | Cl | $-OCH(CH_3)_2$ | $CH_3$ | $CH_3$ |
| Cl | $-OCH_2CH_2O-$ | F | Cl | $-CH_2OCH(CH_3)_2$ | $CH_3$ | $CH_3$ |
| Cl | $-SCH_2CH_2O-$ | F | Cl | $-OCH(CH_3)_2$ | $CH_3$ | $CH_3$ |
| Cl | $-SCH_2CH_2S-$ | F | Cl | $-OCH(CH_3)_2$ | $CH_3$ | $CH_3$ |
| Cl | $-SCH_2CH_2S-$ | F | Cl | $-CH_2OCH(CH_3)_2$ | $CH_3$ | $CH_3$ |
| Cl | $-OCH_2CH_3$ | F | Cl | $-OCH_2CO_2-$ 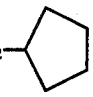 | $CH_3$ | $CH_3$ |
| Cl | $-OCH_2CH_3$ | F | Cl | $-CH{=}CHCO_2CH_3$ | $CH_3$ | $CH_3$ |
| Cl | $-OCH_2CH_3$ | F | Cl | $-SCH_2CO_2-$ 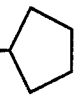 | $CH_3$ | $CH_3$ |
| Cl | $-OCH_2CH_3$ | F | Cl | $-OCH(CH_3)_2$ | $CH_2CH_3$ | $CH_2CH_3$ |
| Cl | $-OCH_2CH_3$ | F | Cl | $-CH_2OCH(CH_3)_2$ | $CH_2CH_3$ | $CH_2CH_3$ |
| Cl | $-OCH_2CH_3$ | F | Cl | $-CO_2CH_3$ | $CH_2CH_3$ | $CH_2CH_3$ |
| Cl | $-OCH_2CH_2O-$ | F | Cl | $-OCH(CH_3)_2$ | $CH_2CH_3$ | $CH_2CH_3$ |
| Cl | $-OCH_2CH_2O-$ | F | Cl | $-CH_2OCH(CH_3)_2$ | $CH_2CH_3$ | $CH_2CH_3$ |
| Cl | $-OCH_2CH_2O-$ | F | Cl | $-CO_2CH_3$ | $CH_2CH_3$ | $CH_2CH_3$ |
| Cl | $-SCH_2CH_2S-$ | F | Cl | $-OCH(CH_3)_2$ | $CH_2CH_3$ | $CH_2CH_3$ |
| Cl | $-SCH_2CH_2S-$ | F | Cl | $-CH_2OCH(CH_3)_2$ | $CH_2CH_3$ | $CH_2CH_3$ |
| Cl | $-SCH_2CH_2S-$ | F | Cl | $-CO_2CH_3$ | $CH_2CH_3$ | $CH_2CH_3$ |
| $-OCH_3$ | $-OCH_2CH_3$ | F | Cl | $-OCH(CH_3)_2$ | $CH_2CH_3$ | $CH_2CH_3$ |
| $-OCH_3$ | $-OCH_2CH_3$ | F | Cl | $-CH_2OCH(CH_3)_2$ | $CH_2CH_3$ | $CH_2CH_3$ |
| $-SCH_3$ | $-OCH_2CH_3$ | F | Cl | $-OCH(CH_3)_2$ | $CH_2CH_3$ | $CH_2CH_3$ |
| $-SCH_3$ | $-OCH_2CH_3$ | F | Cl | $-CH_2OCH(CH_3)_2$ | $CH_2CH_3$ | $CH_2CH_3$ |
| Cl | $-OCH_2CH_3$ | H | Cl | $-OCH(CH_3)_2$ | $CH_3$ | $CH_3$ |
| Cl | $-OCH_2CH_3$ | H | Cl | $-CH_2OCH(CH_3)_2$ | $CH_3$ | $CH_3$ |
| Cl | $-OCH_2CH_3$ | H | Cl | $-CO_2CH_3$ | $CH_3$ | $CH_3$ |
| Cl | $-OCH_2CH_2O-$ | H | Cl | $-OCH(CH_3)_2$ | $CH_3$ | $CH_3$ |
| Cl | $-OCH_2CH_2O-$ | H | Cl | $-CH_2OCH(CH_3)_2$ | $CH_3$ | $CH_3$ |
| Cl | $-SCH_2CH_2S-$ | H | Cl | $-OCH(CH_3)_2$ | $CH_3$ | $CH_3$ |
| Cl | $-SCH_2CH_2S-$ | H | Cl | $-CH_2OCH(CH_3)_2$ | $CH_3$ | $CH_3$ |
| Cl | $-SCH_2CH_2S-$ | H | Cl | $-CO_2CH_3$ | $CH_3$ | $CH_3$ |
| $-OCH_3$ | $-OCH_2CH_3$ | H | Cl | $-OCH(CH_3)_2$ | $CH_3$ | $CH_3$ |
| $-OCH_3$ | $-OCH_2CH_3$ | H | Cl | $-CH_2OCH(CH_3)_2$ | $CH_3$ | $CH_3$ |
| $-SCH_3$ | $-OCH_2CH_3$ | H | Cl | $-OCH(CH_3)_2$ | $CH_3$ | $CH_3$ |
| $-SCH_3$ | $-OCH_2CH_3$ | H | Cl | $-CH_2OCH(CH_3)_2$ | $CH_3$ | $CH_3$ |

SYNTHESIS

In general, compounds according to the invention having the formula

Z—Ar wherein Ar is

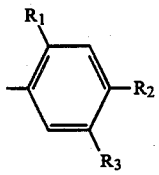

and wherein Z, $R_1$, $R_2$, and $R_3$ are as previously defined, can be prepared by first reacting a compound having the formula

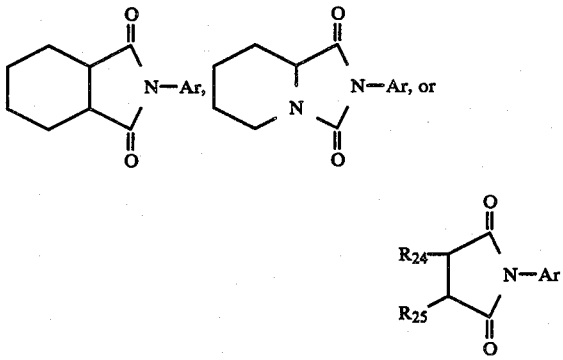

with an excess of phosphorus pentachloride containing a catalytic amount of phosphorus oxychloride;

then reacting the product thereof with a nucleophilic reactant, HW, wherein W is as previously defined, and a proton acceptor under conditions sufficient to convert said first compound to a second compound having the formula

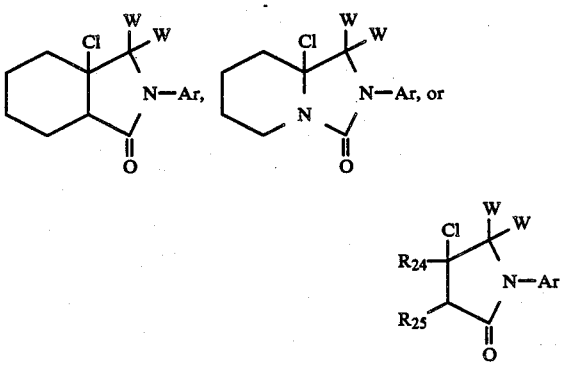

then reacting the product containing said second moiety with a nucleophilic reactant, X, wherein X is as previously defined under conditions sufficient to obtain said anilide compound.

The starting materials shown above are well known to the art with the exception of those wherein $R_3$ is a substituted or unsubstituted phosphono group or those wherein $R_3$ is a substituted methylene group. The former can be made as disclosed in copending application Ser. No. 870,118, now abandoned, commonly assigned. The latter can be made as disclosed in copending application Ser. No. 869,914, commonly assigned. Both applications are herein incorporated by reference.

As a specific example, the following reaction scheme is illustrated specifically for tetrahydrophthalimides, although it is generally applicable to syntheses where Z is a different heterocycle.

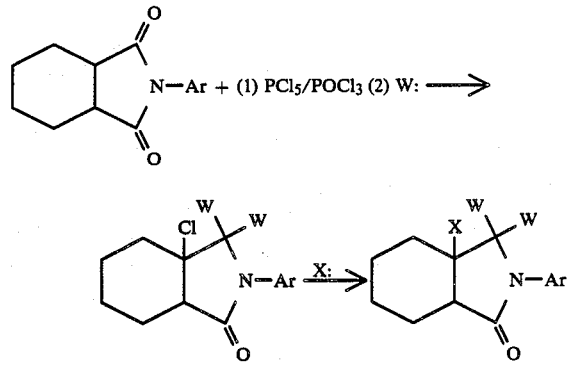

wherein X, W, and Ar are as previously defined.

The above reaction can be carried out in the absence of solvent by heating the imide with an excess of phosphorous pentachloride containing a catalytic amount of phosphorous oxychloride to a temperature of 100°-125° C. After a few hours the volatiles can be removed under reduced pressure, the residue can be treated with excess nucleophile, HW, and a proton acceptor such as pyridine, triethylamine, or the like can be added. The product is a $\beta$-chloro amide ketal, which can be further modified by treatment with nucleophiles, X, to yield any of the desired compounds of this invention.

When Z is derived from a hexahydrophthalimide or succinimide ring system, the aryl tetrahydrophthalimide intermediates required in the above reaction scheme can be synthesized by condensing the appropriate aniline with hexahydrophthalic anhydride or the appropriately substituted succinic anhydride as follows:

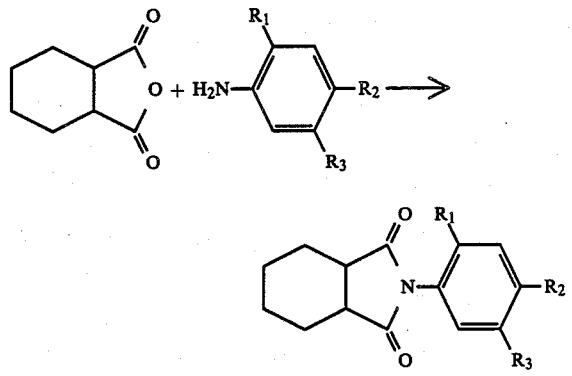

The above reaction can be carried out in the absence of any solvent or in a solvent such as acetic acid, methanol, toluene, or dioxane at a temperature from 60°-200° C. with azeotropic removal of the water formed in the reaction.

Compounds according to the invention having an imidazolidinedione moiety as Z can be prepared by reacting an isocyanate derived from the aniline shown above with ethyl pipecolinate followed, if necessary to promote cyclization, by treatment with an aqueous or alcoholic base solution, as follows:

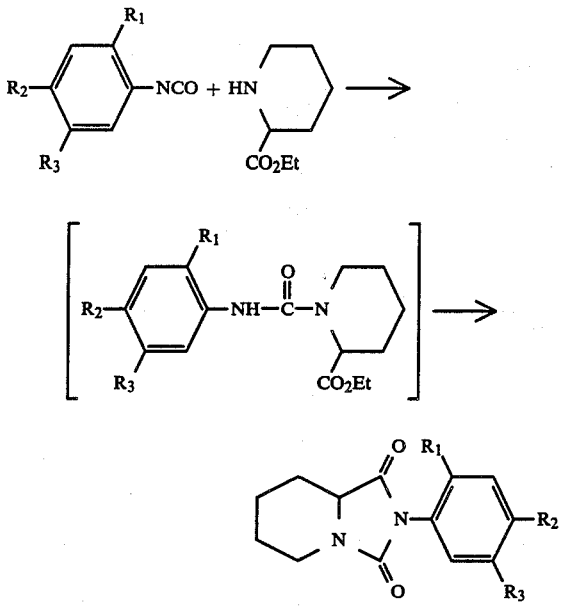

The reaction with the isocyanate can be carried out in any inert organic solvent such as dichloromethane, ethyl ether, toluene, and so forth, and may be run at a temperature from 20°–125° C. Bases which can be employed for the cyclization include both inorganic bases such as sodium hydride and sodium hydroxide, and organic bases such as triethylamine. The cyclization can be run in a variety of organic solvents, including ethanol, dichloromethane, or toluene at a temperature of 20°–100° C.

This invention further provides a novel synthesis route specifically for preparing 3,4,5,6-tetrahydrophthalimides having the structure

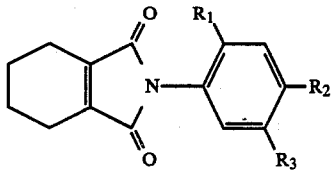

wherein $R_1$, $R_2$, and $R_3$ are as previously defined. Compounds falling within the above generic formula have been prepared as disclosed in numerous publications, e.g. U.S. Pat. No. 4,431,822, by reacting an aniline of the formula

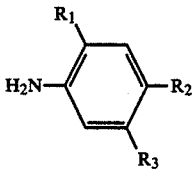

sometimes referred to herein simply as "the aniline") with 3,4,5,6-tetrahydrophthalic anhydride

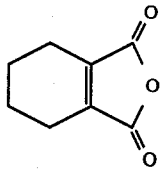

Using the compounds of the present invention as intermediates, the above tetrahydrophthalimides can be prepared by first synthesizing the hexahydrophthalimide and then converting the hexahydrophthalimide to the tetrahydrophthalimide, as follows:

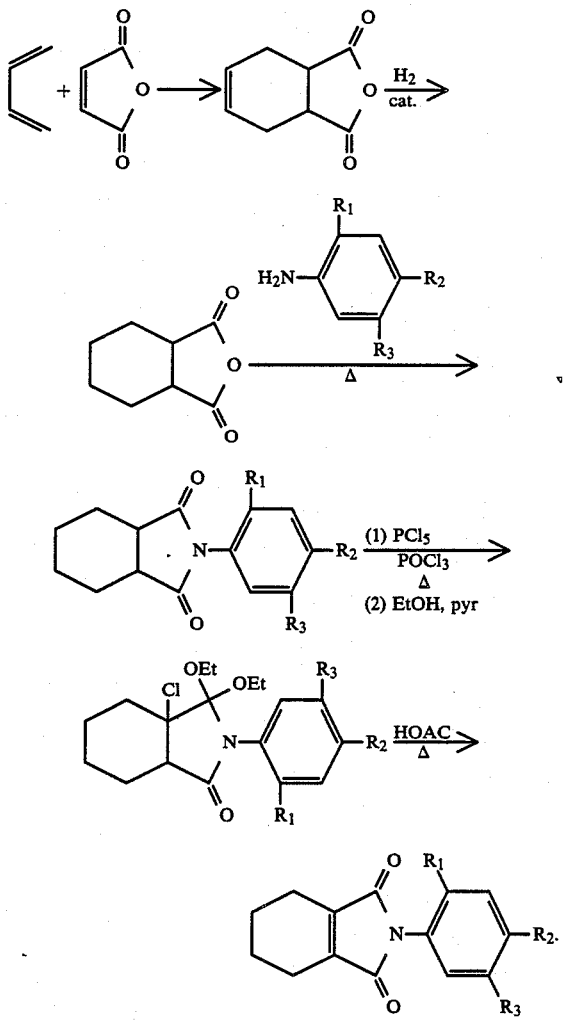

In the above reaction scheme, the synthesis of hexahydrophthalic anhydride via the condensation of butadiene and maleic anhydride followed by catalytic reduction, a well known reaction, is shown for the sake of completeness. Hexahydrophthalic anhydride, whether synthesized or purchased commercially, can be reacted with the aniline by heating in the range of 75°–150° C. to form the corresponding hexahydrophthalimide. The hexahydrophthalimide thus formed can then be converted to the corresponding amide ketal by heating with an excess of $PCl_5$ and a catalytic amount of $POCl_3$ followed by the addition of a proton acceptor and a nucleophilic reactant, HW, e.g. an alcohol. By refluxing in a suitable acidic solvent (acetic acid being shown for purposes of exemplification) for 2–6 hrs. at temperatures of 75°–150° C., the desired tetrahydrophthalimide can be obtained, generally as a mixture with the α-chlorohexahydrophthalimide. Refluxing for longer periods of time and at higher temperatures improves the yield of the N-aryltetrahydrophthalimide (see Example III). The N-aryl-3,4,5,6-tetrahydrophthalimides are potent herbicides well described in the patent literature. The above route affords a direct route to these herbicides from relatively inexpensive starting materials.

The following examples illustrate specific procedures useful in preparing the compounds of this invention.

EXAMPLE I

N-(2-fluoro-4-chloro-5-diethoxyphosphonylphenyl)-3,3-diethoxy-4-chlorohexahydrophthalamide A 250 ml round bottom flask was equipped with a magnetic stirrer and reflux condenser with $N_2$ inlet. The flask was charged with 4.8 g (0.012 mol) of N-(2-fluoro-4-chloro-5-dichlorophosphonyl)phenylhexahydrophthalimide (prepared by condensing diethyl 2-chloro-4-fluoro-5-aminophenyl phosphonate with cyclohexane-1,2-dicarboxylic anhydride followed by cleavage of the phosphonate ester with bromotrimethylsilane and conversion to the phosphonyl chloride with refluxing thionyl chloride), 5.0 g of phosphorous pentachloride, and 0.5 g of phosphorous oxychloride. The mixture was heated to 100° C. under $N_2$ for 3.5 hours. The reaction mixture was cooled to room temperature and the volatiles removed under vacuum. To the residue was added 40 ml of 1:1 pyridine-ethanol solution, and the mixture stirred 12 hours at room temperature. Most of the solvent was removed under reduced pressure, the residue was taken up in $CH_2Cl_2$, washed with water, 5% HCl, and water again. The solvent was removed to give an oil which was recrystallized from hexane-ethyl acetate to give 2.4 g (38% yield) of N-(2-fluoro-4-chloro-5-diethoxyphosphonophenyl)-3,3-diethoxy-4-chlorohexahydrophthalamide, mp 103°–105° C.

| Anal. | % C | % H | % N |
|---|---|---|---|
| Calc. | 50.20 | 5.94 | 2.66 |
| Found | 49.73 | 5.73 | 2.51 |

EXAMPLE II

N-(2-fluoro-4 chloro-5-isopropoxyphenyl)-3,3-diethoxy 4-chlorohexahydrophthalimide A pressure bottle was charged with 1.01 g (0.003 mol) of N-(2 fluoro- 4-chloro-5-isopropoxyphenyl) -3,4,5,6-tetrahydrophthalimide (see U.S. Pat. No. 4,431,822 for the preparation of this compound), 0.10 g of 5% Pt/C, and 60 ml of methylene chloride, placed on a Paar apparatus, and hydrogenated at 40 psi for 3 hours. Thin layer chromatography showed that the hydrogenation of the double bond was complete. The reaction mixture was filtered through Celite, and solvent removed from the filtrate to give 1.0 g (100% yield) of N-(2-fluoro-4 chloro-5-isopropoxyphenyl)hexahydrophthalimide as a white solid.

A 250 ml round bottom flask was equipped with a magnetic stirring bar and a reflux condenser with $N_2$ inlet. The flask was charged with 1.0 g (0.003 mol) of N-(2-fluoro 4-chloro 5-isopropoxyphenyl)hexahydrophthalimide, 1.25 g (6.00 mmol) phosphorous pentachloride, and 2 drops of phosphorous oxychloride. This mixture was heated under $N_2$ with an oil bath to 100° C. for 4 hours, and then the residue placed on a vacuum pump overnight. The reaction mixture was placed in an ice water bath and treated dropwise with a solution of 5 ml of ethanol and 5 ml of pyridine. The mixture was stirred 3 hours at room temperature. The reaction mixture was concentrated under reduced pressure, taken up in $CH_2Cl_2$, washed with water, then 5% HCl, then water, dried ($MgSO_4$), and the solvent removed to leave an orange oil. This oil was purified by flash chromatography through silica gel using $CH_2Cl_2$ to give 0.60 g (45% yield) of N- (2-fluoro-4-chloro-5-isopropoxyphenyl)-3,3-diethoxy-4-chlorohexahydrophthalimide.

| Anal. | % C | % H | % N |
|---|---|---|---|
| Calc. | 56.25 | 6.29 | 3.12 |
| Found | 56.20 | 6.51 | 3.64 |

EXAMPLE III

Use of N-(2-fluoro-4-chloro-5-diethoxyphosphonylphenyl)-3,3-diethoxy-4-chlorohexahydrophthalamide for the synthesis of N-(2-fluoro-4-chloro-5-diethoxyphosphonylphenyl-4-chlorohexahydrophthalimide and N-(2-fluoro-4-chloro-5-diethoxyphosphonylphenyl)-3,4,5,6-tetrahydrophthalimide A 50 ml round bottom flask equipped with a magnetic stirring bar and reflux condenser with nitrogen inlet was charged with 1.3 g (0.0025 mol) of N- (2-fluoro 4-chloro-5-diethoxyphosphonylphenyl)-3,3-diethoxy-4-chlorohexahydrophthalimide and 15 ml of glacial acetic acid. The mixture was heated to reflux for two days, then cooled to room temperature and poured into ice water. The mixture was extracted with ethyl acetate and the extracts combined and washed three times with water. The extracts were dried ($MgSO_4$) and the solvent removed under reduced pressure. Thin layer chromatography of the residue (1:1 hexane-ethyl acetate) showed two components at $R_f$ 0.45 and 0.35. These components were separated by flash chromatography (60:40 hexane-ethyl acetate) to give 300 mg of the $R_f$ 0.45 component and 300 mg of the $R_f$ 0.35 component. NMR showed the $R_f$ 0.45 component to be N- (2-fluoro-4-chloro-5-diethoxyphosphonylphenyl)-4-chloro-hexahydrophthalimide. NMR $CDCl_3$: δ1.35 (t,6H); 1.25–1.75 (m,4H); 1.80–2.58 (m,4H); 3.30 (5,1H); 3.88–4.52 (quintet, 4H); 7.21–7.60 (g,1H); 7.73–8.25 (q,1H).

NMR of the $R_f$ 0.35 component revealed that this material was N-(2-fluoro-4-chloro-5-diethoxy-phosphonylphenyl)-3,4,5,6-tetrahydrophthalimide NMR ($CDCl_3$: 1.33 (t,3H); 1.60–2.0 (m,4H); 2.09–2.63 (m,4H); 4.21 (quintet, 4H); 7.38 (g,1H); 7.95 (q,1H).

Herbicide Activity

The biological efficacy and selectivity of compounds representative of this invention as terrestrial herbicides were evaluated as preemergence herbicides and as postemergence herbicides. The test plants were mustard, teaweed, velvetleaf, morninglory and pigweed. For the preemergence test, seeds of the type of plants as shown in Table II were sown in fresh soil. In the preemergence test, the soil was sprayed with a solution of the test compound immediately after the seeds were planted. The solution was about a 1% by weight solution of the test compound in acetone. The compounds were applied at a rate as indicated in Table II.

Approximately three weeks after spray applications, the herbicidal activity of the compound was determined by visual observation of the treated area in comparison with untreated controls. These observations are reported on a scale of 0 to 100% control of plant growth.

In the postemergence test the soil and developing plants were sprayed about two weeks after the seeds were sown. The compounds were applied at a rate as indicated in Table I for each test compound from about a 1% by weight solution of the test compound in acetone. The postemergence herbicidal activity was measured in the same way as the preemergence activity at three weeks following treatment.

The results of both the preemergence and postemergence test are set forth in Tables I and II below. Abbreviations used for test crops: soybeans (SB), corn (CN), wheat (WH), and rice (RI). Abbreviations used for test weeds: morningglory (MG), mustard (MU), teaweed (TW), velvetleaf (VE), and pigweed (PW).

Table I shows herbicidal data for two compounds of this invention which have exhibited excellent broadleaf weed control and good crop selectivity at low application rates in postemergent treatments.

TABLE I

Post-emergent Herbicidal Activity/Crop Selectivity of Novel Anilide Herbicide Derivatives

| Structure | Rate (lb/A) | SB | CN | WH | RI | MG | Mu | TW | Ve | Pw |
|---|---|---|---|---|---|---|---|---|---|---|
| | | % Injury | | | | | % Control | | | |
| 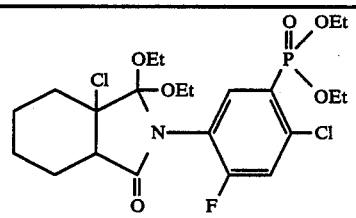 | 0.25 | 21 | 10 | 0 | 0 | 21 | 11 | 100 | 100 | 100 |
| 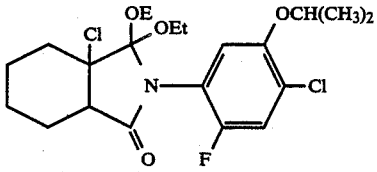 | 0.25 | 11 | 0 | 0 | 0 | 78 | 100 | 65 | 100 | 100 |

Note: —Et = —$C_2H_5$

Table II shows pre emergent efficacy data for the same compounds shown in Table I.

TABLE II

Pre-emergent[3] Herbicidal Activity/Crop Selectivity of Novel Anilide Herbicide Derivatives

| | Rate (lb/A) | SB | CN | WH | RI | MG | MU | TW | Ve | Pw |
|---|---|---|---|---|---|---|---|---|---|---|
| | | % Injury | | | | % Control | | | | |
| 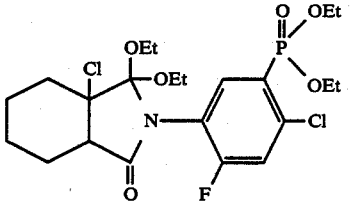 | 0.25 | 11 | 0 | 19 | 0 | 100 | 0 | 30 | 100 | 0 |
| 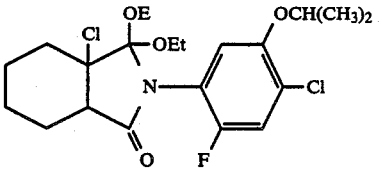 | 0.25 | 2 | 0 | 6 | 11 | 19 | 76 | 91 | 100 | 100 |

[1]Crop Species: SB = soybean CN = corn WH = wheat RI = rice
[2]Weed Species: MB = morningglory MU = wild mustard TW = teaweed Ve = velvetleaf PW = pigweed
[3]Seeds treated with a 1:1 acetone-water solution of the test compounds.

It will be understood that the plant species employed in the above tests are merely representative of a wide variety of plants that can be controlled by the use of the compounds of this invention. The compounds contemplated in this invention may be applied as postemergent and preemergent herbicides according to methods known to those skilled in the art. Compositions containing the compounds as the active ingredient will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agent.

The choice of dispersing and emulsifying agents and the amount employed is dictated by the nature of the composition and the ability of the agent to facilitate the dispersion of the compound. Generally, it is desirable to use as little of the agent as is possible, consistent with the desired dispersion of the compound in the spray so that rain does not re-emulsify the compound after it is applied to the plant and wash if off the plant. Nonionic, anionic, amphoteric or cationic dispersing and emulsifying agents may be employed; for example, the condensation products of alkylene oxides with phenol and organic acids, alkyl aryl sulfonates, complex ether alchols, guaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the compound contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active ingredient per acre.

The herbicides contemplated herein have a good margin of safety in that when used in sufficient amount to control broadleaf weeds they do not burn or injure the crop and they resist weathering which includes wash-off caused by rain, decomposition by ultra violet light, oxidation, or hydrolysis in the presence of moisture or, at least such decomposition, oxidation, and hydrolysis as would materially decrease the desirable characteristic of the compound or impart undesirable characteristic for instance, phytotoxicity, to the compound. It will be appreciated that the compounds of this invention can also be used in combination with other biologically active compounds.

Those skilled in the art will readily appreciate that many modifications are possible in the exemplary embodiments without materially departing from the teachings and advantages of this invention.

We claim:

1. Anilide compounds having the structure:

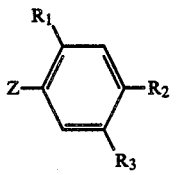

wherein $R_1$ and $R_2$ contain not more than 10 aliphatic carbon atoms and are independently:

hydrogen, halogen, ($C_1$–$C_3$) alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl groups;

$R_3$ is a substituted heteroatom or a substituted carbon atom, or a substituted or unsubstituted, branched or straight chain containing 2 or more carbon atoms or heteroatoms in any combination; and Z is:

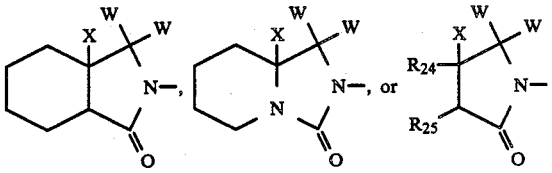

wherein:

$R_{24}$ and $R_{25}$ are independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenythio, alkynylthio, cycloalkylthio, cycloalkenylthio, alkoxycarbonylalkoxy, alkoxycarbonylalkylthio, haloalkoxy, haloalkylthio, alkoxyalkoxy, alkylthioalkoxy, alkoxyalkylthio, alkylthioalkylthio, cyanoalkoxy, alkylcarbonylalkoxy alkylcarbonylalkylthio phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by one or more alkyl, alkynyl, phenyl, or phenyl substituted by one or more halogen, lower alkyl, lower alkoxy, cyano, nitro, alkylthio, or haloalkyl groups, aminocarbonylalkylthio wherein the amino group may be substituted by one or more alkyl, alkenyl, phenyl, or phenyl substituted by one or more halogen, lower alkyl, lower alkoxy, cyano, nitro, alkylthio, or haloalkyl groups, or a five or six-member ring containing one or two oxygen, nitrogen, or sulfur atoms; and X contains not more than 10 aliphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

2. Anilide compounds having the structure:

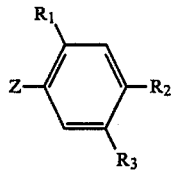

wherein:

$R_1$ and $R_2$ contain not more than 10 aliphatic carbon atoms and are independently:

hydrogen, halogen, ($C_1$–$C_3$) alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl groups;

$R_3$ is:

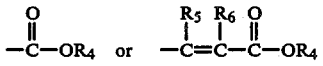

wherein:

$R_4$ contains not more than 10 aliphatic carbon atoms and is:

hydrogen, $C_1$–$C_{10}$ alkyl, alkenyl cycloalkyl, cycloalkenyl, or alkynyl, alkoxycarbonylalkyl, alkoxycarbonyl, alkylcarbonyl, alkenylcarbonyl, alkynylcarbonyl, cycloalkylcarbonyl, phenyl, phenylcarbonyl or phenoxycarbonyl wherein the phenyl ring of each may be substituted by one or more halogen, lower alkyl, lower alkoxy, cyano, nitro, alkylthio, or haloalkyl groups, $R_5$ and $R_6$ are independently hydrogen or $C_1$–$C_3$ alkyl;

Z is:

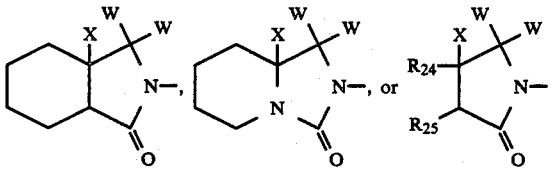

wherein:

$R_{24}$ and $R_{25}$ are independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenylthio, alkynylthio, cycloalkylthio, cycloalkenylthio, alkoxycarbonylalkoxy, alkoxycarbonyl alkylthio, haloalkoxy, haloalkylthio, alkoxyalkoxy, alkylthioalkoxy, alkoxyalkylthio, alkylthioalkylthio, cyanoalkoxy, alkylcarbonylalkoxy alkylcarbonylalkylthio phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by one or more alkyl, alkynyl, phenyl, or phenyl which may be substituted by one or more halogen, lower alkyl, lower alkoxy, cyano, nitro, alkylthio, or haloalkyl groups, aminocarbonylalkylthio wherein the amino group may be substituted by one or more alkyl, alkenyl, phenyl, or phenyl substituted by one or more halogen, lower alkyl, lower alkoxy, cyano, nitro, alkylthio, or haloalkyl groups, or a five or six-member ring containing one or two oxygen, nitrogen, or sulfur atoms; and X contains not more than 10 aliphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

3. Anilide compounds having the structure:

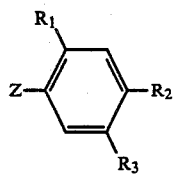

wherein:

$R_1$ and $R_2$ contain not more than 10 aliphatic carbon atoms and are independently:

hydrogen, halogen, ($C_1$–$C_3$ alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl groups, $R_3$ is —$OR_4$, wherein $R_4$ is:

hydrogen, $C_1$–$C_{10}$ alkyl, alkenyl cycloalkyl, cycloalkenyl, or alkynyl, alkoxycarbonylalkyl, alkoxycarbonyl, alkylcarbonyl alkenylcarbonyl, alkynylcarbonyl, cycloalkylcarbonyl, phenyl, phenylcarbonyl, or phenoxycarbonyl wherein the phenyl ring of each may be substituted by one or more halogen, lower alkyl, lower alkoxy, cyano, nitro, alkylthio, or haloalkyl groups, Z is:

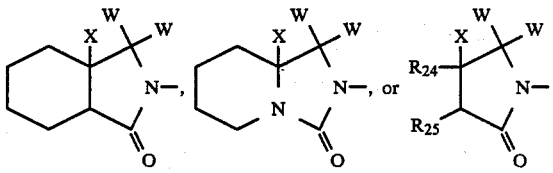

wherein:

$R_{24}$ and $R_{25}$ are independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenylthio, alkynylthio, cycloalkylthio, cycloalkenylthio, alkoxycarbonylalkoxy, alkoxycarbonylalkythio, haloalkoxy, haloalkylthio, alkoxyalkoxy, alkylthioalkoxy, alkoxyalkylthio, alkylthioalkylthio, cyanoalkoxy, alkylcarbonylalkoxy alkylcarbonylalkylthio phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by one or more alkyl, alkynyl, phenyl, or phenyl substituted by one or more halogen, lower alkyl, lower alkoxy, cyano, nitro, alkylthio, or haloalkyl groups, aminocarbonylalkylthio wherein the amino group may be substituted by one or more alkyl, alkenyl, phenyl, or phenyl substituted by one or more halogen, lower alkyl, lower alkoxy, cyano, nitro, alkylthio, or haloalkyl groups, or a five or six-member ring containing one or two oxygen, nitrogen, or sulfur atoms; and X contains not more than 10 aliphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

4. Anilide compounds having the structure:

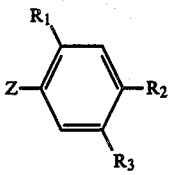

wherein:

$R_1$ and $R_2$ contain not more than 10 aliphatic carbon atoms and are independently:

hydrogen, halogen, ($C_1$–$C_3$ alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl groups;

$R_3$ is

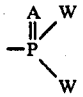

wherein A is oxygen or sulfur;

Z is:

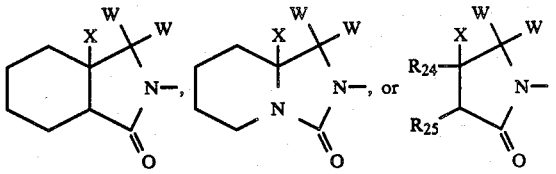

wherein:

$R_{24}$ and $R_{25}$ are independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenylthio, alkynylthio, cycloalkylthio, cycloalkenylthio, alkoxycarbonylalkoxy, alkoxycarbonylalkylthio, haloalkoxy, haloalkylthio, alkoxyalkoxy, alkylthioalkoxy, alkoxyalkylthio, alkylthioalkylthio, cyanoalkoxy, alkylcarbonylalkoxy alkylcarbonylalkylthio phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by one or more alkyl, alkynyl, phenyl, or phenyl substituted by one or more halogen, lower alkyl, lower alkoxy, cyano, nitro, alkylthio, or haloalkyl groups, aminocarbonylalkylthio wherein the amino group may be substituted by one or more alkyl, alkenyl, phenyl, or phenyl substituted by one or more halogen, lower alkyl, lower alkoxy, cyano, nitro, alkylthio, or haloalkyl groups, a five or six-member ring containing one or two oxygen, nitrogen, or sulfur atoms; and X contains not more than 10 aliphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

5. Anilide compounds having the structure:

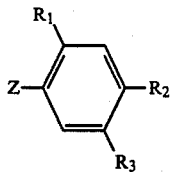

wherein:

$R_1$ and $R_2$ contain not more than 10 aliphatic carbon atoms and are independently:

hydrogen, halogen, ($C_1$–) alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl $R_3$ is:

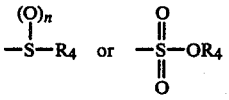

wherein n is an integer from 0–2; and $R_4$ is:

hydrogen, $C_1$–$C_{10}$ alkyl, alkenyl cycloalkyl, cycloalkenyl or alkynyl, alkoxycarbonylalkyl, alkoxycarbonyl, alkylcarbonyl alkenylcarbonyl, alkynylcarbonyl, cycloalkylcarbonyl, phenyl, phenylcarbonyl, or phenxoycarbonyl wherein the phenyl ring of each may be substituted by one or more halogen, lower alkyl, lower alkoxy, cyano, nitro, alkylthio, or haloalkyl groups, Z is:

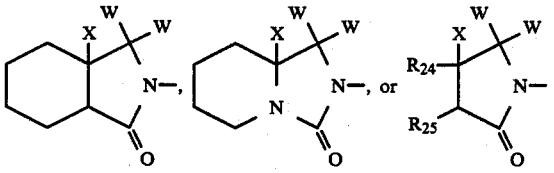

wherein:

$R_{24}$ and $R_{25}$ are independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenylthio, alkynylthio, cycloalkylthio, cycloalkenylthio, alkoxycarbonylalkoxy, alkoxycarbonylalkylthio, haloalkoxy, haloalkylthio, alkoxyalkoxy, alkylthioalkoxy, alkoxyalkylthio, alkylthioalkylthio, cyanoalkoxy, alkylcarbonylalkoxy alkylcarbonylalkylthio phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by one or more alkyl, alkynyl, phenyl, or phenyl substituted by one or more halogen, lower alkyl, lower alkoxy, cyano, nitro, alkylthio, or haloalkyl groups, aminocarbonylalkylthio wherein the amino group may be substituted by one or more alkyl, alkenyl, phenyl, or phenyl substituted by one or more halogen, lower alkyl, lower alkoxy, cyano, nitro, alkylthio, or haloalkyl groups, or a five or six-member ring containing one or two oxygen, nitrogen, or sulfur atoms; and X contains not more than 10 aliphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

6. Anilide compounds having the structure:

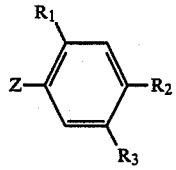

wherein:

$R_1$ and $R_2$ contain not more than 10 aliphatic carbon atoms and are independently:

hydrogen, halogen, ($C_1$—$C_3$) alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl groups;

$R_3$ is:

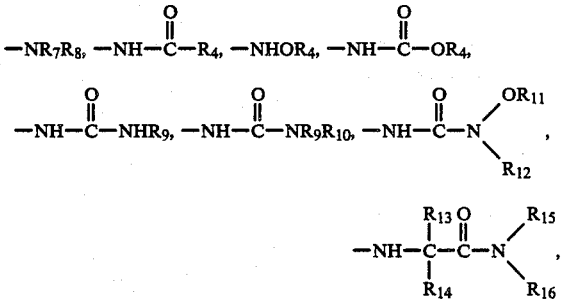

wherein $R_4$ is:

hydrogen, $C_1$–$C_{10}$ alkyl, alkenyl cycloalkyl, cycloalkenyl, or alkynyl, alkoxycarbonylalkyl, alkoxycarbonyl, alkylcarbonyl, alkenylcarbonyl, alkynylcarbonyl, cycloalkylcarbonyl, phenyl, phenylcarbonyl, or phenoxycarbonyl wherein the phenyl ring of each may be substituted by one or more halogen, lower alkyl, lower alkoxy, cyano, nitro, alkylthio, or haloalkyl groups, $R_7$ and $R_8$ are independently hydrogen, $C_1$–$C_6$ alkyl, alkenyl, alkynyl, cycloakyl, mono or dialkylaminocarbonylalkyl or, taken together, $R_7$ and $R_8$ form a five- or six-membered heterocyclic ring containing one to three oxygen, nitrogen, or sulfur atoms in any combination;

$R_9$ and $R_{10}$ are independently hydrogen, $C_1$–$C_4$ alkyl or, taken together, $R_9$ and $R_{10}$ form a five or six membered ring;

$R_{11}$ is $C_1$–$C_3$ alkyl;

$R_{12}$ is hydrogen or $C_1$–$C_3$ alkyl;

$R_{13}$ and $R_{14}$ are independently hydrogen or $C_1$–$C_3$ alkyl; and $R_{15}$ and $R_{16}$ are independently hydrogen, $C_1$–$C_3$ alkyl or $C_1$–$C_3$ alkoxy;

Z is:

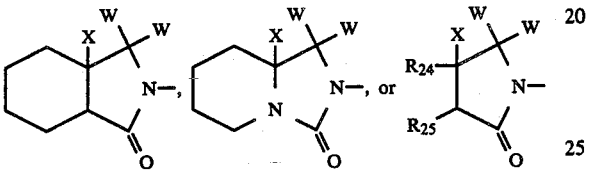

wherein:

$R_{24}$ and $R_{25}$ are independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenylthio, alkynylthio, cycloalkylthio, cycloalkenylthio, alkoxycarbonylalkoxy, alkoxycarbonylalkylthio, alkylthio, haloalkoxy, haloalkylthio, alkoxyalkoxy, alkylthioalkoxy, alkoxyalkylthio, alkylthioalkylthio, cyanoalkoxy, alkylcarbonylalkoxy alkylcarbonylalkylthio phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by one or more alkyl, alkynyl, phenyl, or phenyl substituted by one or more halogen, lower alkyl, lower alkoxy, cyano, nitro, alkylthio, or haloalkyl groups, aminocarbonylalkylthio wherein the amino group may be substituted by one or more alkyl, alkenyl, phenyl, or phenyl substituted by one or more halogen, lower alkyl, lower alkoxy, cyano, nitro, alkylthio, or haloalkyl groups, or a five or six member ring containing one or two oxygen, nitrogen, or sulfur atoms; and X contains not more than 10 liphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

7. Anilide compounds having the structure:

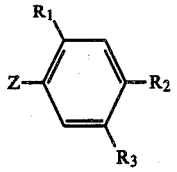

wherein:

$R_1$ and $R_2$ contain not more than 10 aliphatic carbon atoms and are independently:

hydrogen, halogen, $C_1$–$C_3$) alkyl, ($C_1$–$C_3$) alkoxy, trifluoromethyl, phenoxy or benzyloxy, either of which may be substituted by halogen, lower alkyl, lower alkoxy, cyano, nitro, alkylthio, or haloalkyl groups;

$R_3$ is:

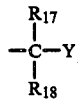

wherein $R_{17}$ and $R_{18}$ are independently hydrogen $C_1$–$C_8$ alkyl, or halogen;

Y is:

hydrogen, halogen, cyano, alkyl, cyloalkyl, cycloalkyl alkyl, alkenyl, cycloalkenyl, cloalkenyl alkyl, alkynyl, alkoxy, alkenyloxy, alkynyloxy, cycloalkyloxy, cycloalkenyloxy, alkoxycarbonylalkoxy, alkoxycarbonylalkylthio, alkoxycarbonyloxy, alkoxycarbonylamino, alkylthiocarbonyloxy, alkylaminothiocarbonyloxy, haloalkoxy, haloalkylthio, alkoxyalkoxy (e.g., $-OCH_2CH_2OCH_3$), alkylthioalkoxy (e.g., $-OCH_2CH_2OCH_3$) koxyalkylthio (e.g., $-SCH_2CH_2OCH_3$), alkylthioalkylthio, cyanoalkoxy, alkylcarbonylalkoxy, cycloalkoxycarbonylalkoxy, alkylcarbonylalkylthio, alkoxycarbonylalkylamino, alkoxycarbonylalkyl alkylamino, alkylsulfinyl, alkylsulfonyl, alkoxycarbonylalkylsufinyl, alkoxycarbonylalkylsulfonyl, alkylcarbonylalkylamino, phenoxy, phenylthio, phenylcarbonylalkoxy, phenoxycarbonylaalkoxy, phenylcarbonylalkylthio, phenoxycarbonylalkylthior, or phenylcarbonylalkylamino wherein the phenyl ring in each may be substituted by one or more halogen, lower alkyl, lower alkoxy, cyano, nitro, alkylthio, or haloalkyl groups, phenylsulfinyl or phenylsulfonyl wherein the phenyl ring in either may be substituted by one or more halogen, lower alkyl, lower alkoxy, cyano, nitro, alkylthio, or haloalkyl groups, amino substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group is substituted by one or more alkyl, alkenyl, phenyl or phenyl substituted by one or more halogen, lower alkyl, lower alkoxy, cyano, nitro, alkylthio, or haloalkyl groups, aminocarbonylalkylthio wherein the amino group is substituted by one or more alkyl, alkenyl, phenyl, or phenyl substituted by one or more halogen, lower alkyl, lower alkoxy, cyano, nitro, alkylthio, or haloalkyl groups, aminocarbonylalkylamino wherein each of the amino groups is independently substituted by one or more alkyl, alkenyl, alkynyl, phenyl or phenyl substituted by one or more halogen, lower alkyl, lower alkoxy, cyano, nitro, alkylthio, or haloalkyl groups, or any of the following functional grouos:

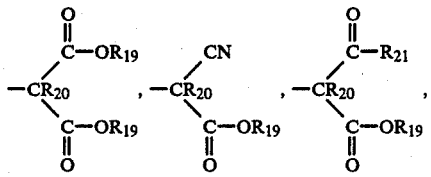

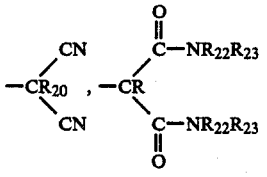

wherein:

$R_{19}$ is $C_1$–$C_6$ alkyl, cycloalkyl, alkenyl, alkynyl, or cycloakenyl;

$R_{20}$ and $R_{21}$ are independently hydrogen, $C_1$–$C_6$ alkyl, cycloalkyl, alkenyl, alkynyl, cycloalkenyl, phenyl, or phenyl substituted by one or more halogen, lower alkyl, lower alkoxy, cyano, nitro, alkylthio, or haloalkyl groups, $R_{22}$ and $R_{23}$ are independently hydrogen, $C_1$–$C_6$ alkyl, cycloalkyl, alkenyl, alkynyl, or cycloalkenyl;

or wherein Y is any five- or six membered heterocycle containing from one to three oxygen, en, or sulfur atoms Z is:

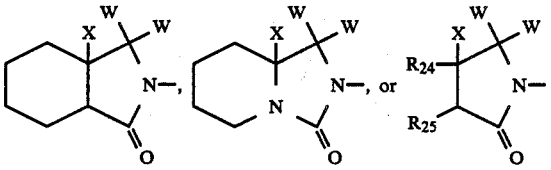

wherein:

$R_{24}$ and $R_{25}$ are independently $C_1$–$C_6$ alkyl, alkenyl, or alkynyl;

W contains not more than 10 aliphatic carbon atoms and is:

alkoxy, cycloalkoxy, alkenyloxy, alkynyloxy, cycloalkenyloxy, alkylthio, alkenylthio, alkynylthio, cycloalkylthio, cycloalkenylthio, alkoxycarbonylalkoxy, alkoxycarbonylalkylthio, haloalkoxy, haloalkylthio, alkoxyalkoxy, alkylthioalkoxy, alkoxyalkylthio, alkylthioalkylthio, cyanoalkoxy, alkylcarbonylalkoxy alkylcarbonylalkylthio phenoxy, phenoxycarbonylalkoxy, phenylcarbonylalkoxy, or phenylcarbonylalkylthio wherein the phenyl ring in each may be substituted by one or more halogen, lower alkyl, lower alkoxy, cyano, nitro, alkylthio, or haloalkyl groups in any combination, amino which may be substituted by one or more alkyl, alkenyl, alkynyl, phenyl, or phenyl substituted by one or more halogen, lower alkyl, lower alkoxy, cyano, nitro, alkylthio, or haloalkyl groups, aminocarbonylalkoxy wherein the amino group may be substituted by one or more alkyl, alkynyl, phenyl which may be substituted by one or more halogen, lower alkyl, lower alkoxy, cyano, nitro, alkylthio, or haloalkyl groups, aminocarbonylalkylthio wherein the amino group may be substituted by one or more alkyl, alkenyl, phenyl, or phenyl substituted by one or more halogen, lower alkyl, lower alkoxy, cyano, nitro, alkylthio, or haloalkyl groups, or a five or six-member ring containing one or two oxygen, nitrogen, or sulfur atoms; and X contains not more than 10 aliphatic carbon atoms and is halogen, hydroxy, alkylcarbonyloxy, alkoxycarbonyloxy, alkylcarbonylthio, alkoxycarbonylthio, alkoxy, alkenyloxy, alkynyloxy, amino, alkylamino, dialkylamino, mercapto, alkylthio, alkenylthio, alkylsulfinyl or alkylsulfonyl.

8. The compounds of claim 1, wherein Z is

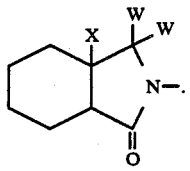

9. The compounds of claim 1, wherein Z is

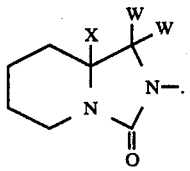

10. The compounds of claim 1, wherein Z is

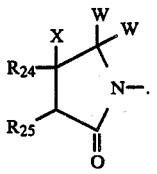

11. A compound as defined in claim 1, which is N-(2 fluoro 4 chloro 5 diethoxyphosphonylphenyl) 3,3-diethoxy-4-chlorohexahydrophthalamide.

12. A compound as defined in claim 1, which is N-(2 fluoro-4 chloro-5-isopropoxy phenyl) 3,3-diethoxy-4-chlorohexahydrophthalamide.

13. A herbicide composition comprising an acceptable carrier and a herbicidally effective amount of a compound as defined in claim 1.

14. A herbicide composition comprising an acceptable carrier and a herbicidally effective amount of a compound as defined in claim 2.

15. A herbicide composition comprising an acceptable carrier and a herbicidally effective amount of a compound as defined in claim 3.

16. A herbicide composition comprising an acceptable carrier and a herbicidally effective amount of a compound as defined in claim 4.

17. A herbicide composition comprising an acceptable carrier and a herbicidally effective amount of a compound as defined in claim 5.

18. A herbicide composition comprising an acceptable carrier and a herbicidally effective amount of a compound as defined in claim 6.

19. A herbicide composition comprising an acceptable carrier and a herbicidally effective amount of a compound as defined in claim 7.

20. A herbicide composition comprising an acceptable carrier and a herbicidally effective amount of a compound as defined in claim 8.

21. A herbicide composition comprising an acceptable carrier and a herbicidally effective amount of a compound as defined in claim 9.

22. A herbicide composition comprising an acceptable carrier and a herbicidally effective amount of a compound as defined in claim 10.

23. A herbicide composition comprising an acceptable carrier and a herbicidally effective amount of a compound as defined in claim 11.

24. A herbicide composition comprising an acceptable carrier and a herbicidally effective amount of a compound as defined in claim 12.

25. A method of controlling weeds, which comprises subjecting said weeds to a herbicidally effective amount of a compound as defined in claim 1.

26. A method of controlling weeds, which comprises subjecting said weeds to a herbicidally effective amount of a compound as defined in claim 2.

27. A method of controlling weeds, which comprises subjecting said weeds to a herbicidally effective amount of a compound as defined in claim 3.

28. A method of controlling weeds, which comprises subjecting said weeds to a herbicidally effective amount of a compound as defined in claim 4.

29. A method of controlling weeds, which comprises subjecting said weeds to a herbicidally effective amount of a compound as defined in claim 5.

30. A method of controlling weeds, which comprises subjecting said weeds to a herbicidally effective amount of a compound as defined in claim 6.

31. A method of controlling weeds, which comprises subjecting said weeds to a herbicidally effective amount of a compound as defined in claim 7.

32. A method of controlling weeds, which comprises subjecting said weeds to a herbicidally effective amount of a compound as defined in claim 8.

33. A method of controlling weeds, which comprises subjecting said weeds to a herbicidally effective amount of a compound as defined in claim 9.

34. A method of controlling weeds, which comprises subjecting said weeds to a herbicidally effective amount of a compound as defined in claim 35. A method of controlling weeds, which comprises subjecting said weeds to a herbicidally effective amount of a compound as defined in claim 36. A method of controlling weeds, which comprises subjecting said weeds to a herbicidally effective amount of a compound as defined in claim 37. A process of making anilide compounds of th formula Z—Ar which comprises:

first reacting a compound having the formula

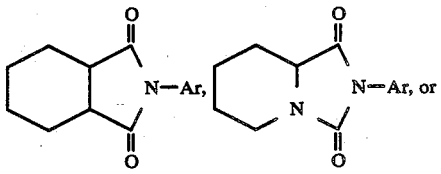

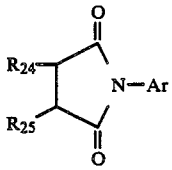

with an excess of phosphorus pentachloride containing a catalytic amount of phosphorus oxychloride;

then reacting the product thereof with a nucleophile, W:, and a proton acceptor under conditions sufficient to convert said first compound to a second compound having the formula

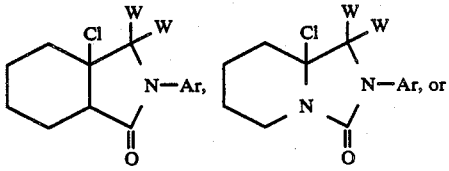

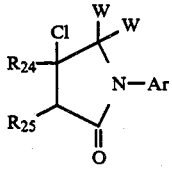

then reacting said second compound with a nucleophile, X:, under conditions sufficient to obtain said anilide compound, wherein: Ar is the group

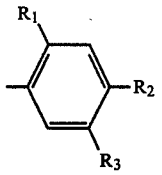

$R_1$, $R_2$, $R_3$, W and X are as defined and wherein in claim 1.

38. A process of making anilide compounds of the formula

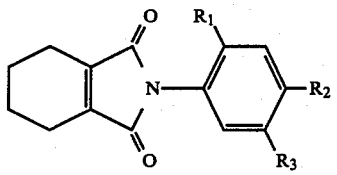

comprising making a first compound of the formula

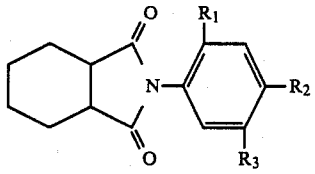

heating said first compound with an excess of $PCl_5$ and a catalytic amount of POC13. followed by adding a nucleophilic reactant, HW, and a proton acceptor, thereby producing a second compound of the formula

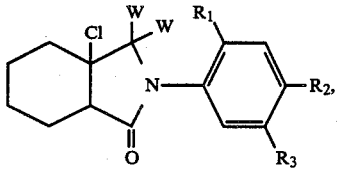

and heating said second compound in an acidic solvent to produce said anilide compound, and wherein $R_1$, $R_2$, $R_3$ and W are as defined in claim 1.

* * * * *